(12) United States Patent
Huang et al.

(10) Patent No.: US 11,497,555 B2
(45) Date of Patent: Nov. 15, 2022

(54) FLEXIBLE MICROWAVE ABLATION ANTENNA AND MICROWAVE ABLATION NEEDLE EMPLOYING SAME

(71) Applicant: Surgnova Healthcare Technologies (Zhejiang) Co., Ltd., Cixi (CN)

(72) Inventors: Wenxing Huang, Beijing (CN); Dezhi Zhan, Beijing (CN); Limin Tian, Beijing (CN); Hui Li, Beijing (CN)

(73) Assignee: SURGNOVA HEALTHCARE TECHNOLOGIES (ZHEJIANG) CO., LTD., Zhejiang (CN)

( * ) Notice: Subject to any disclaimer, the term of this patent is extended or adjusted under 35 U.S.C. 154(b) by 707 days.

(21) Appl. No.: 16/289,584

(22) Filed: Feb. 28, 2019

(65) Prior Publication Data

US 2020/0069368 A1   Mar. 5, 2020

Related U.S. Application Data

(63) Continuation of application No. PCT/CN2016/102867, filed on Oct. 21, 2016.

(30) Foreign Application Priority Data

Aug. 31, 2016   (CN) .......................... 201610797834.9

(51) Int. Cl.
*A61B 18/18* (2006.01)
*A61B 18/00* (2006.01)

(52) U.S. Cl.
CPC ...................... *A61B 18/1815* (2013.01); *A61B 2018/00023* (2013.01); *A61B 2018/00148* (2013.01);
(Continued)

(58) Field of Classification Search
CPC ................ A61B 18/18; A61B 18/1815; A61B 2018/1838; A61B 2018/1861;
(Continued)

(56) References Cited

U.S. PATENT DOCUMENTS

| 5,314,466 A | 5/1994 | Stern et al. |
| 6,451,014 B1 | 9/2002 | Wakikaido et al. |

(Continued)

FOREIGN PATENT DOCUMENTS

| CN | 1784183 A | 6/2006 |
| CN | 103732171 A | 4/2014 |

(Continued)

OTHER PUBLICATIONS

International Search Report dated May 4, 2017 in connection with International App. No. PCT/CN2016/102867.
(Continued)

*Primary Examiner* — Thomas A Giuliani
(74) *Attorney, Agent, or Firm* — Hamre, Schumann, Mueller & Larson, P.C.

(57) ABSTRACT

A flexible microwave ablation antenna and a microwave ablation needle including the same are disclosed. The flexible microwave ablation antenna including: a radiator for transmitting microwave for ablation; a coaxial cable for propagating the microwave for ablation generated by a microwave generator to the radiator; wherein the flexible microwave ablation antenna is bendable. Preferably, an annular composite structure is disposed around a periphery of the coaxial cable to suppress the electromagnetic wave from propagating along the coaxial cable in a reverse direction. The annular composite structure includes an annular non-metallic layer and an annular metallic layer surrounding the annular non-metallic layer. The annular metallic layer is electrically insulated from the coaxial cable.

16 Claims, 2 Drawing Sheets

(52) U.S. Cl.
CPC ............... *A61B 2018/00494* (2013.01); *A61B 2018/00541* (2013.01); *A61B 2018/00577* (2013.01); *A61B 2018/183* (2013.01); *A61B 2018/1861* (2013.01); *A61B 2018/1869* (2013.01)

(58) Field of Classification Search
CPC ...... A61B 2018/1869; A61B 2018/183; A61B 2018/00023; A61B 2018/00577
USPC ............................. 606/33; 607/101, 154, 156
See application file for complete search history.

(56) References Cited

U.S. PATENT DOCUMENTS

| | | | |
|---|---|---|---|
| 7,033,352 | B1 | 4/2006 | Gauthier et al. |
| 10,987,152 | B2* | 4/2021 | Brannan ............... A61B 18/149 |
| 2003/0125730 | A1* | 7/2003 | Berube ............... A61B 18/1492 |
| | | | 606/45 |
| 2007/0203480 | A1 | 8/2007 | Mody et al. |
| 2011/0066144 | A1* | 3/2011 | Bonn ................. A61B 18/1815 |
| | | | 29/600 |
| 2011/0130750 | A1 | 6/2011 | Ormsby et al. |
| 2012/0259326 | A1* | 10/2012 | Brannan .......... A61B 17/00234 |
| | | | 606/33 |

FOREIGN PATENT DOCUMENTS

| | | |
|---|---|---|
| CN | 105596079 A | 5/2016 |
| CN | 105816240 A | 8/2016 |
| CN | 206587036 U | 10/2017 |

OTHER PUBLICATIONS

Extended European Search Report dated Mar. 10, 2020 in connection with European App. No. 16914816.0.

* cited by examiner

FLEXIBLE MICROWAVE ABLATION ANTENNA AND MICROWAVE ABLATION NEEDLE EMPLOYING SAME

CROSS-REFERENCE TO RELATED APPLICATIONS

This application is a continuation of International Application No. PCT/CN2016/102867 filed on Oct. 21, 2016 and entitled "Flexible Microwave Ablation Antenna and Microwave Ablation Needle Including the Same". The '867 international application claims priority benefit to Chinese Application No. 201610797834.9 filed on Aug. 31, 2016 also entitled "Flexible Microwave Ablation Antenna and Microwave Ablation Needle Including the Same". The '867 international application is hereby incorporated by reference herein in its entirety.

FIELD OF THE INVENTION

The present disclosure relates to a field of microwave therapy equipment, and more particularly to a flexible microwave ablation antenna and a microwave ablation needle including the same.

In recent years, microwave ablation technology has developed rapidly. It mainly utilizes a thermal effect of microwave in polar molecules, such as water, to allow a lesion area to reach a very high temperature instantly and allow tissue to coagulate, dehydrate and necrose, thereby achieving a purpose for treatment. Early microwave ablation technology is mainly employed in a treatment for liver cancer. The current microwave ablation technology has begun to be applied to more tumor ablation for human organs, such as kidney cancer, thyroid cancer, colon cancer, lung cancer, and so on. For the ablation of lung cancer, it is mainly treated by a minimally invasive surgery in which a hard ablation needle is used to subcutaneously puncture into the tumor area for ablation. However, due to the particularity of the lung organ, the use of a hard needle for subcutaneous puncture for microwave ablation is likely to cause air in lungs to leak into chest cavity, thereby causing postoperative complications such as pneumothorax and pneumonia.

SUMMARY OF INVENTION

In some embodiments, a flexible microwave ablation antenna, can include: a radiator for transmitting a microwave signal for ablation; and a coaxial cable for propagating the microwave signal for ablation generated by the microwave generator to the radiator, wherein the flexible microwave ablation antenna is bendable and has a minimum curvature radius of 10 to 80 mm, preferably 40 to 60 mm, and further preferably 50 mm.

In some embodiments, a microwave ablation needle is provided, wherein the microwave ablation needle includes the flexible microwave ablation antenna as described above; and wherein the microwave ablation needle is able to bend, deform, and deeply go into inside of a human body to be treated following a natural channel in the human body.

DETAILED DESCRIPTION OF ILLUSTRATIVE EMBODIMENT(S)

Figure 1:
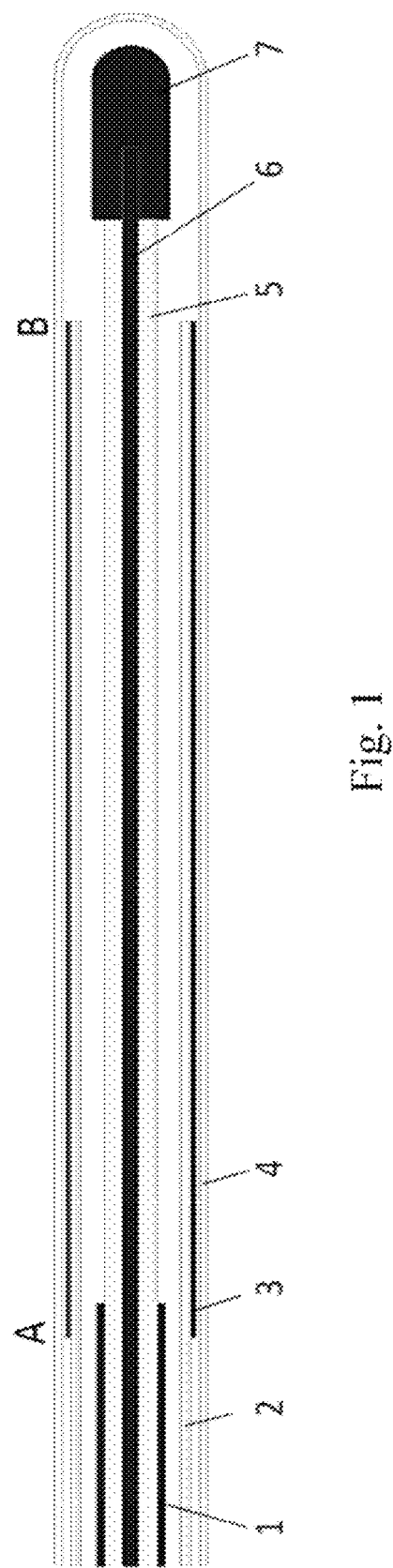
FIG. 1 is a structural schematic view of a needle head of an ablation needle according to the present disclosure.

The present disclosure will be further described in detail below with reference to the specific embodiments and the drawings in order to make the objects, technical solutions and advantages of the disclosure clearer and more understandable.

The term "flexible" in the present disclosure is recited relative to "rigid", and has a meaning that an object is moderately bendable, preferably arbitrarily bendable and capable of being restored. The bending is preferably defined by a minimum curvature radius, for example, a minimum curvature radius of 10-80 mm, preferably of 40-60 mm, and further preferably of 50 mm.

Specifically, the present disclosure discloses a flexible microwave ablation antenna and a microwave ablation needle including the same. The flexible microwave ablation antenna includes: a radiator for transmitting a microwave signal for ablation; and a coaxial cable for propagating the microwave signal for ablation generated by a microwave generator to the radiator, wherein the flexible microwave ablation antenna as a whole presents a flexibility performance, that is, the flexible microwave ablation antenna is bendable and has a minimum curvature radius of 10 to 80 mm, preferably 40 to 60 mm, and further preferably 50 mm so as to be able to bend, deform and deeply go into inside of a human body to be treated following a natural channel in the human body. For example, when used to treat a lung tumor, the flexible microwave ablation antenna can deeply go into the lungs following trachea and bronchus; and when used to treat colon cancer or colon tumors, the flexible microwave ablation antenna is able to deeply go into inside of the human body following anus and intestines.

In addition, an annular composite structure is disposed around a periphery of the coaxial cable so as to suppress electromagnetic wave from propagating along the coaxial cable in a reverse direction opposite to the metal cap. The annular composite structure can include an annular non-metallic layer and an annular metallic layer surrounding the annular non-metallic layer. The annular metallic layer can be electrically insulated from the coaxial cable. In some preferred embodiments, the annular composite structure may only include the above two layers, or may further include more layers, such as another non-metallic layer surrounding the annular metallic layer.

The material of the annular metallic layer can be copper, iron, aluminum, gold, silver, palladium, platinum, tin, nickel, zinc or an alloy thereof, and is preferably copper. The annular metallic layer can have a thickness in the range of 0.001 mm to 0.1 mm and a length in the range of one quarter to three quarters of a wavelength of the microwave transmitted by the flexible microwave ablation antenna and propagating in the tissue. Preferably, for a flexible microwave ablation antenna with a frequency of 2.45 GHz, the annular metallic layer has a length of 5 mm to 25 mm.

The flexible microwave ablation antenna can further include a cooling passage for cooling the radiator. In some preferred embodiments, the cooling passage is capable of delivering a cooling medium to a foremost end of the radiator to cool the entire radiator. The cooling passage can be of a non-metallic flexible material such as PEEK (polyether ether ketone) or PTFE (polytetrafluoroethylene) material.

In some preferred embodiments, the annular metallic layer is formed by wrapping/adhering a metal foil processed into a thin layer on/to an outer wall of the cooling passage disposed around the periphery of the coaxial cable, or is formed on an outer wall of the cooling passage disposed around the periphery of the coaxial cable by a sputtering process, a plating process or a chemical plating process. The annular metallic layer and the non-metallic cooling passage together form the annular composite structure or a part of the annular composite structure.

In some preferred embodiments, the annular metallic layer is formed on an inlet passage of the cooling passage, and may not completely cover the cooling passage in length. For example, in some embodiments, an end of the cooling passage near the radiator is not covered by the annular metallic layer with a length of at least 0.5 mm.

In some embodiments, the radiator can be a metal cap, an extension of a core of the coaxial cable, or a core of the coaxial cable with soldering tin.

The flexible microwave ablation antenna can further include an outer shroud for protecting the internal structure from short circuits. The outer shroud can be of a non-metallic flexible material, for example preferably of PEEK or PTFE material.

The disclosure further discloses a microwave ablation needle, which includes the flexible microwave ablation antenna as described above. The microwave ablation needle is capable of bending, deforming and deeply going into inside of the human body to be treated following a natural channel in the human body.

Figure 2:
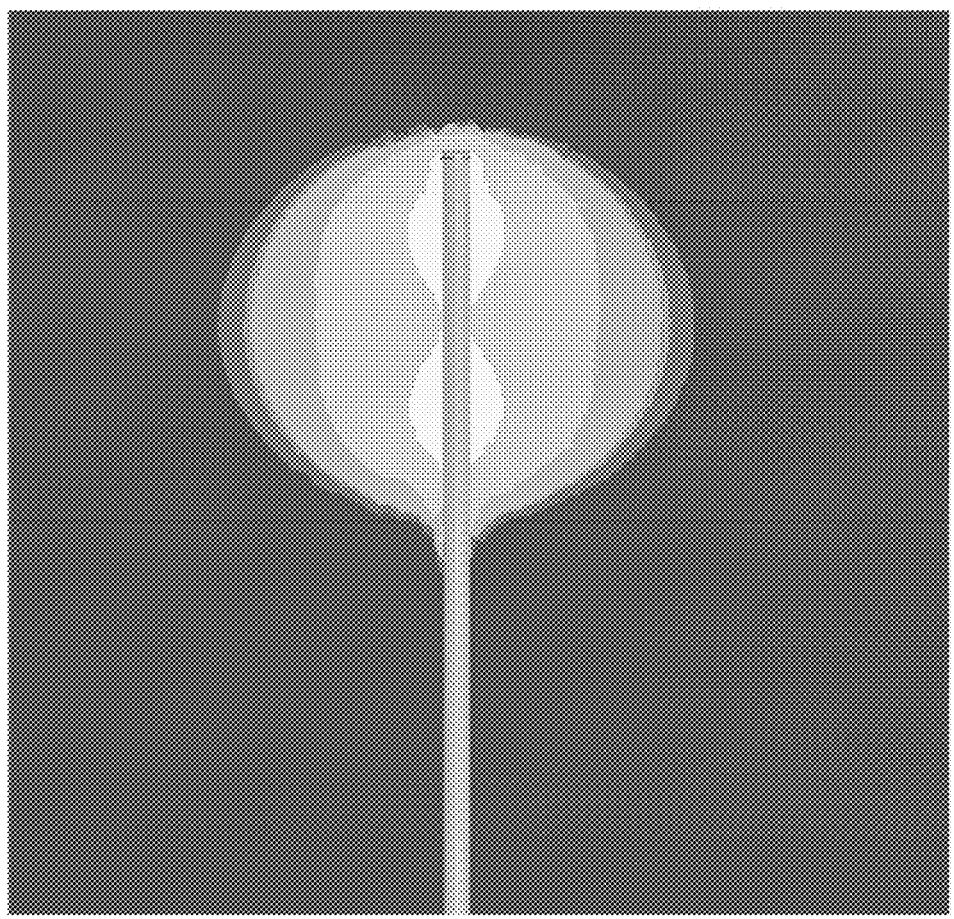
FIG. 2 is a simulation diagram of an ablation area for the needle head of the ablation needle according to the present disclosure.

It can be known from the above technical solutions that, the flexible microwave ablation antenna and the microwave ablation needle according to the present disclosure can have the following beneficial effects:

(1) The ablation needle can have a good flexibility and can deeply go into the lungs through the respiratory tract for ablation, which avoids perforation in the lungs, thereby reducing a risk of postoperative complications such as pneumothorax and pneumonia;

(2) The microwave can be effectively suppressed from propagating backward along a needle rod of the ablation needle; the microwave can be concentrated/focused on a needle head of the ablation needle to obtain an ideal ablation area, which results in a good ablation effect; and the ablation area can be a spherical area, as shown in a simulation diagram of the ablation area in FIG. 2;

(3) The circulating water can be ensured to reach the needle head of the ablation needle so that the ablation needle is sufficiently cooled, avoiding too high a temperature of the ablation needle that may otherwise damage or scald the human body.

The technical solutions of the present disclosure are further explained below in connection with the accompanying drawings and specific embodiments.

FIG. 1 is a cross-sectional view of a needle head of a microwave ablation needle according to a preferable embodiment of the present disclosure, wherein the needle head of a microwave ablation needle includes flexible coaxial cable metal braided layer 1; water inlet passage 2; metal foil, thin metal ring or metal coating 3; outer shroud 4; dielectric layer of a flexible coaxial cable 5; inner conductor of the flexible coaxial cable 6; and metal cap 7 welded to the inner conductor of the coaxial cable.

In some embodiments, water inlet passage 2 and outer shroud 4 are made of a non-metallic flexible material such as Peek or PTFE. In some embodiments, the length of thin metal foil 3 wrapping around a terminal end of water inlet passage 2 proximate to metal cap 7 is about half the wavelength of the microwave in the tissue (with an effective range of ±50%). For a microwave of 2.45 GHz and human lung tissue, the length of the metal foil or thin metal ring 3 is about 15 mm. The thickness of the metal foil or thin metal ring 3 can be between and inclusive of 0.001 mm and 0.1 mm, preferably the thinnest thickness that is available. By doing so, the water outlet passage between water inlet passage 2 and outer shroud 4 can be ensured to be unobstructed, and water inlet passage 2 still has good flexibility after being wrapped by thin metal foil 3.

A relative distance between a terminal end of the flexible coaxial cable metal braided layer 1 proximate to metal cap 7 and a first end A of metal foil 3 remote to metal cap 7, which is a distance by which the terminal end of flexible coaxial cable metal braided layer 1 proximate to metal cap 7 are separated from the first end A of metal foil 3 remote to metal cap 7 or a length of an overlapping portion between flexible coaxial cable metal braided layer 1 and metal foil 3, is less than $\frac{1}{10}$ of the wavelength of the microwave in the tissue. A terminal end of dielectric layer 5 of the flexible coaxial cable proximate to metal cap 7 closely abuts against metal cap 7, and a relative distance between the terminal end of dielectric layer 5 proximate to metal cap 7 and a second end B of metal foil 3 proximate to metal cap 7 is less than $\frac{1}{5}$ of the wavelength of the microwave in the tissue. In some embodiments, a length of metal cap 7 is $\frac{1}{10} \sim \frac{1}{4}$ of the wavelength of the microwave in the tissue.

In some embodiments in which thin metal ring 3 is adopted, thin metal ring 3 can be embedded on the water inlet passage, and a terminal end of water inlet passage 2 proximate to metal cap 7 is at least 0.5 mm longer than the terminal end of flexible coaxial cable metal braided layer 1 and the first end A of thin metal ring 3. That is, the second end B of thin metal ring 3 proximate to metal cap 7 in this embodiment extends towards metal cap 7 beyond the end of water inlet passage 2 proximate to metal cap 7, and the end of water inlet passage 2 proximate to metal cap 7 extends towards metal cap 7 beyond the first end A of thin metal ring 3 by at least 0.5 mm. In one embodiment, the end of water inlet passage 2 proximate to metal cap 7 extends towards metal cap 7 beyond the end of flexible coaxial cable metal braided layer 1 proximate to metal cap 7 by at least 0.5 mm.

The microwave is mainly radiated from the second end B of metal foil 3, and at the same time, a part of the microwave is leaked from the gap between flexible coaxial cable metal braided layer 1 and metallic layer 3. The microwave radiated from the second end B will partially propagate along a needle rod of the ablation needle. When the microwave propagating along the needle rod of the ablation needle reaches the first end A, its phase position is opposite to the phase position of the microwave leaking from the first end A and they counteract with each other, which suppresses the microwave from continuing propagating along the needle rod. Thus, the microwave energy is concentrated in the vicinity of metal foil 3.

The ablation can be performed by this flexible microwave ablation needle going deeply into the lung tumor area following respiratory tract and lung bronchus. In at least some embodiments, this method of ablation will not cause a pneumothorax and no, or at least minimum, wound will be left.

The cooling medium for the microwave ablation needle can be circulating water, such as medical purified water or physiological saline.

In addition, the microwave ablation needle may not include the radiator in the form of metal cap, but the radiator may be replaced by directly soldering tin on the core of the coaxial cable, or an extension of the core of the coaxial cable may be directly used (without metal braided layer wrapped) as a radiator;

The objects, the technical solutions and the advantages of the present disclosure have been described in detail in connection with the specific embodiments above. However, it should be appreciated that the above-described embodiments are all exemplary and the present disclosure is not limited thereto. Any modifications, equivalent substitutions and improvements made within the spirit and principle of the present disclosure should fall within the scope of the present disclosure.

What is claimed is:

1. A flexible microwave ablation antenna, comprising:
a radiator for transmitting microwave for ablation;
a coaxial cable for propagating said microwave for ablation generated by a microwave generator to said radiator;
wherein said flexible microwave ablation antenna is bendable and has a minimum curvature radius of 10 mm to 80 mm;
wherein an annular composite structure is disposed around a periphery of said coaxial cable so as to suppress electromagnetic wave from propagating along said coaxial cable in a reverse direction;
wherein said annular composite structure comprises an annular non-metallic layer and an annular metallic layer surrounding said annular non-metallic layer, said annular metallic layer being electrically insulated from said coaxial cable; and
wherein said annular metallic layer has a length in a range of one quarter to three quarters of a wavelength of said microwave transmitted by said flexible microwave ablation antenna and propagated in tissue;
wherein the coaxial cable comprises a metal braided layer, the metal braided layer comprises an end, the annular metallic layer comprises two opposite ends, and in a direction along the coaxial cable, the end of the metal braided layer is located between the two opposite ends of the annular metallic layer.

2. The flexible microwave ablation antenna according to claim 1,
wherein said minimum curvature radius is of 40 mm to 60 mm.

3. The flexible microwave ablation antenna according to claim 1,
wherein said minimum curvature radius is of 50 mm.

4. The flexible microwave ablation antenna according to claim 1,
wherein a material of said annular metallic layer is copper, iron, aluminum, gold, silver, palladium, platinum, tin, nickel, zinc or an alloy thereof.

5. The flexible microwave ablation antenna according to claim 1,
wherein said annular metallic layer has a thickness in a range of 0.001 mm to 0.1 mm.

6. The flexible microwave ablation antenna according to claim 1,
wherein said annular metallic layer has a length of 5 mm to 25 mm for a flexible microwave ablation antenna with a frequency of 2.45 GHz.

7. The flexible microwave ablation antenna according to claim 1,
wherein said flexible microwave ablation antenna further comprises a cooling passage for cooling said radiator.

8. The flexible microwave ablation antenna according to claim 7,
wherein said cooling passage is capable of delivering a cooling medium to a foremost end of said radiator to cool said entire radiator.

9. The flexible microwave ablation antenna according to claim 7,
wherein said cooling passage is of a non-metallic flexible material.

10. The flexible microwave ablation antenna according to claim 9,
wherein said cooling passage is made of PEEK or PTFE material.

11. The flexible microwave ablation antenna according to claim 9,
wherein said annular metallic layer is formed by wrapping/adhering a metal foil processed into a thin layer on/to an outer wall of said cooling passage disposed around the periphery of said coaxial cable, or is formed on an outer wall of said cooling passage disposed around the periphery of said coaxial cable by a sputtering process, a plating process or a chemical plating process; and
wherein said annular metallic layer and said cooling passage of non-metallic material together form said annular composite structure or a part of said annular composite structure.

12. The flexible microwave ablation antenna according to claim 11,
wherein said annular metallic layer is formed on an inlet passage of said cooling passage.

13. The flexible microwave ablation antenna according to claim 1,
wherein said radiator is a metal cap or an extension of a core of said coaxial cable.

14. The flexible microwave ablation antenna according to claim 1,
wherein said flexible microwave ablation antenna further comprises an outer shroud, said outer shroud being of a non-metallic flexible material.

15. The flexible microwave ablation antenna according to claim 14,
wherein said outer shroud is made of PEEK or PTFE material.

16. A microwave ablation needle comprising:
a flexible microwave ablation antenna, wherein said flexible microwave ablation antenna comprises:
a radiator for transmitting a microwave for ablation; and
a coaxial cable for propagating said microwave for ablation generated by a microwave generator to said radiator,
wherein said flexible microwave ablation antenna is bendable and has a minimum curvature radius between 10 mm to 80 mm,
wherein an annular composite structure is disposed around a periphery of said coaxial cable so as to suppress electromagnetic wave from propagating along said coaxial cable in a reverse direction;
wherein said annular composite structure comprises an annular non-metallic layer and an annular metallic layer surrounding said annular non-metallic layer, said annular metallic layer being electrically insulated from said coaxial cable;
wherein said annular metallic layer has a length in a range of one quarter to three quarters of a wavelength of said microwave transmitted by said flexible microwave ablation antenna and propagated in tissue, wherein the coaxial cable comprises a metal braided layer, the metal braided layer comprises an end, the annular metallic layer comprises two opposite ends, and in a direction along the coaxial cable, the end of the metal braided layer is located between the two opposite ends of the annular metallic layer, and wherein said microwave ablation needle is capable of bending, deforming and following a natural channel into a human body to treat said human.

* * * * *